Figure 1:
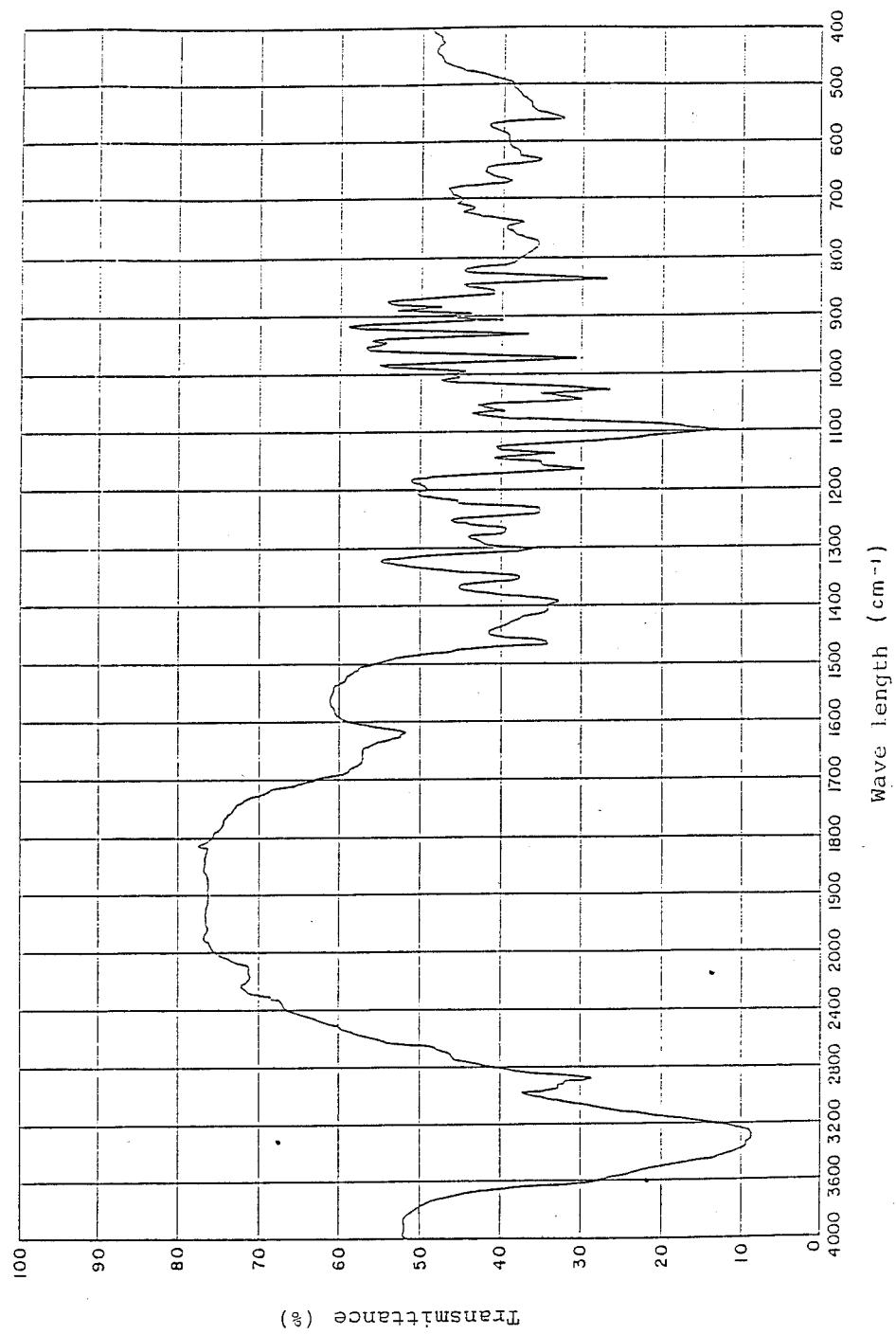

United States Patent

Kameda et al.

[11] Patent Number: 4,923,975
[45] Date of Patent: May 8, 1990

[54] VALIOLAMINE DERIVATIVES AND PRODUCTION THEREOF

[75] Inventors: Yukihiko Kameda, Kanazawa; Satoshi Horii, Sakai, both of Japan

[73] Assignee: Takeda Chemical Industries, Ltd., Osaka, Japan

[21] Appl. No.: 855,407

[22] Filed: Apr. 24, 1986

[30] Foreign Application Priority Data

Apr. 24, 1985 [JP] Japan .................................. 60-89513

[51] Int. Cl.$^5$ .......................... C07H 5/06; C07C 87/36
[52] U.S. Cl. .................................. 536/17.9; 536/17.2; 536/18.7; 564/462
[58] Field of Search .................... 536/17.2, 16.8, 18.7, 536/17.9; 564/462

[56] References Cited

U.S. PATENT DOCUMENTS

| | | | |
|---|---|---|---|
| 4,011,391 | 3/1977 | Horii et al. | 536/16.8 |
| 4,089,947 | 5/1978 | Horii et al. | 536/16.8 |
| 4,595,678 | 6/1986 | Horii et al. | 514/53 |

Primary Examiner—Johnnie R. Brown
Assistant Examiner—Elli Peselev
Attorney, Agent, or Firm—Wegner & Bretschneider

[57] ABSTRACT

A novel valiolamine derivative of the formula (I):

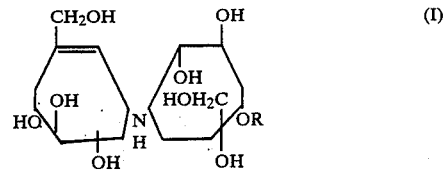

where R stands for hydrogen or $\beta$-D-glucopyranosyl group is useful for a starting material of valiolamine which can be converted to more potent $\alpha$-glucosidase inhibiting compounds. The valiolamine derivative is obtained by cultivating *Streptomyces hygroscopics* in a culture medium and recovering the valiolamine derivative produced and accumulated from the culture broth.

3 Claims, 4 Drawing Sheets

VALIOLAMINE DERIVATIVES AND PRODUCTION THEREOF

This invention relates to a novel valiolamine derivative of the general formula (I);

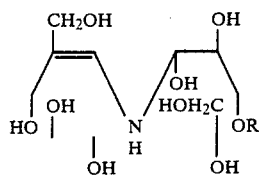

where R stands for hydrogen or β-glucopyranosyl group and a method for production of such valiolamine derivative which comprises cultivating a microorganism which belongs to the genus Streptomyces and is capable of producing the valiolamine derivative in a culture medium to produce and accumulate the valiolamine derivative in the culture broth and recovering the valiolamine derivative from the culture broth.

The present inventors found previously that microorganisms belonging to the genus Streptomyces produced a series of validamycin antibiotics, i.e. validamycins A, B, C, D, E, and F and validoxylamines A and B [See J. Antibiotics 25, 48–53 (1972)]. The chemical structures of these compounds have been estimated as shown in Table 4 based on the results of the further studies.

The inventors have found that among the various compounds obtained by cultivation of the microorganisms under aerobic conditions there exist the novel valiolamine derivatives of the general formula (I) and named the compound of the formula (I) where R is hydrogen "validoxylamine G" and the compound of the formula (I) where R is β-glucopyranosyl group "validamycin G". Validamycin and validoxylamine are sometimes abbreviated as VM and VA, respectively, and so validamycin G and validoxylamine G are VM-G and VA-G, respectively, in this specification.

As shown in Table 4, both VA-G and VM-G contain, as the common moieties, valiolamine [See J. Antibiotics 37,1301–1307 (1984)] and valienamine [See J. Chem. Soc. Chem. Comm. 1972, 476–747] which are bound through a —NH— bond, being different from VM-A, C, D, E, and F and VA-A which contain, as the common moieties, valienamine and validamine [See J. Antibiotics 24,59–63 (1971)] bound through a —NH— bond, and also from VM-B and VA-B which contain, as the common moieties, valienamine and hydroxyvalidamine bound through a -NH- bond [See J. Antibiotics 24,59–63 (1971)]but not valiolamine.

The compounds having the general formula (I) form various acid addition salts. For example, they may form salts of inorganic acid such as sulfuric acid, hydrochloric acid, hydrobromic acid, phosphoric acid, nitric acid, etc. and salts of organic acid such as methanesulfonic acid, p-toluenesulfonic acid, etc. Therefore the compounds of this invention may be recovered or purified as their salts.

Physicochemical properties of validoxylamine G and validamycin G of this invention are as follows: Validoxylamine G
(1) Appearance
white powder
(2) Elementary analysis (molecular formula)

| | $C_{14}H_{25}NO_9 \cdot H_2O$ | | |
|---|---|---|---|
| calculated (%): | C, 45.52; | H, 7.36; | N, 3.79 |
| found (%): | C, 45.83; | H, 7.45; | N, 3.62 |

(3) Specific rotation $[\alpha]_D^{25} + 118.6°$ (c=1, H$_2$O)
(4) UV adsorption spectrum
The aqueous solution does not show any characteristic absorption maximum in the range 200–360 nm, except end absorption.
(5) IR absorption spectrum
The spectrum measured by KBr method is shown in FIG. 1. Wave numbers of main absorption peaks are shown in the following.

Figure 2:
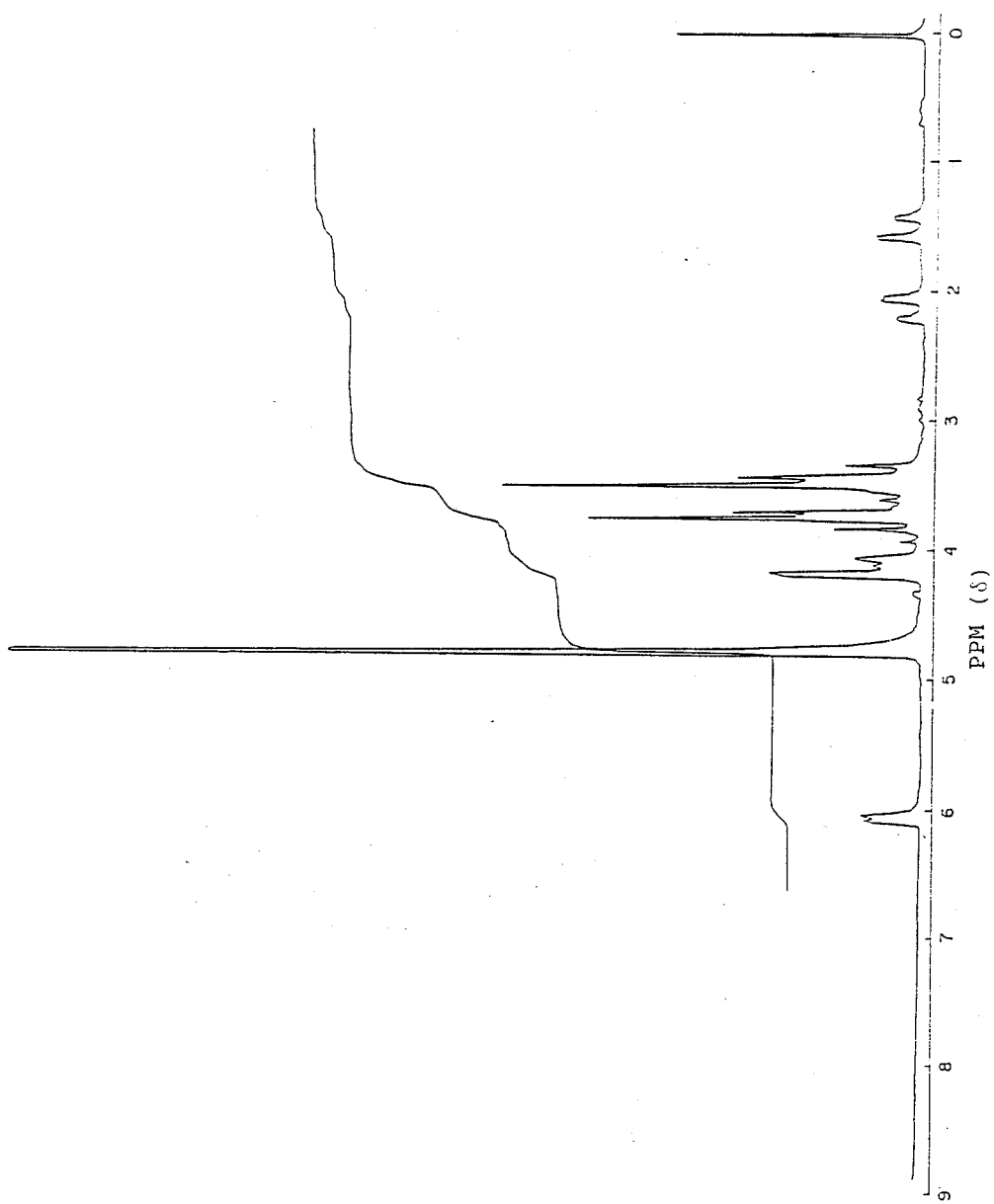

3270, 2880, 1620, 1460, 1390, 1350, 1300, 1265, 1235, 1160, 1140, 1100, 1040, 1025, 975, 930, 905, 895, 885, 860, 835 cm$^{-1}$ (6) $^1$H-NMR/spectrum
FIG. 2 shows the spectrum measured in heavy water at 100 MHz (ppm; internal standard: sodium 2,2-dimethyl-2-silapentane-5-sulfonate (DSS)). The chemical shifts (δ), splitting pattern (s: singlet, d: doublet, t: triplet, dd: double doublet, dt: double triplet, ABq: AB quartet, m: multiplet) and coupling constant (J) were δ1.50 (1H, dd, J=3 Hz, 15.5 Hz, H-6), 2.12 (1H, dd, J=3 Hz, 15.5 Hz, H-6), 3.36–4.20 (12H), and 6.06 (1H, d, J=4.3 Hz, H-2'). Table 1 shows the chemical shifts (δ), splitting pattern and coupling constant (J) of validoxylamine octaacetate obtained by acetylation of 30 validoxylamine G with acetic anhydride-pyridine, in CDCl$_3$ at 400 MHz (ppm; internal standard: tetramethylsilan (TMS)).
(7) 13C-NMR spectrum
The chemical shifts (6) under decoupling conditions in heavy water at 100 MHz (ppm; internal standard: DSS) and splitting pattern under off-resonance conditions are shown in Table 2.
(8) Solubility in solvents
Soluble in water, dimethylsulfoxide, and methanol.
Slightly soluble or insoluble in ethanol, ethyl acetate, chloroform, and acetone.
(9) Color reaction
Reaction with Greig-Leaback reagent: positive
Naphthoresorcinol-sulfuric acid reaction: negative
(10) Thin layer chromatography
Rf values measured on TLC plate: silica gel 60F$_{254}$ (produced by Merck & Co.) developed with 1-PrOH-AcOH-H$_2$O (4:1:1) (developing solvent I) or 1-BuOH-MeOH-CHCl$_3$-28%NH$_4$OH (4:5:2:5) (developing solvent II) are listed in Table 3.
Validamycin G
(1) Appearance white powder
(2) Elementary analysis (molecular formula)

| | $C_{20}H_{35}NO_{14} \cdot H_2O$ | | |
|---|---|---|---|
| calculated (%): | C, 45.19; | H, 7.01; | N, 2.63 |
| found (%): | C, 45.31; | H, 7.19; | N, 2.47 |

(3) Specific rotation
$[\alpha]_D^{25} + 52.8°$ (c=1, H$_2$O)
(4) UV absorption spectrum
The aqueous solution does not show any characteristic absorption maximum in the range 200–360 nm, except end absorption.

(5) IR absorption spectrum

Figure 3:
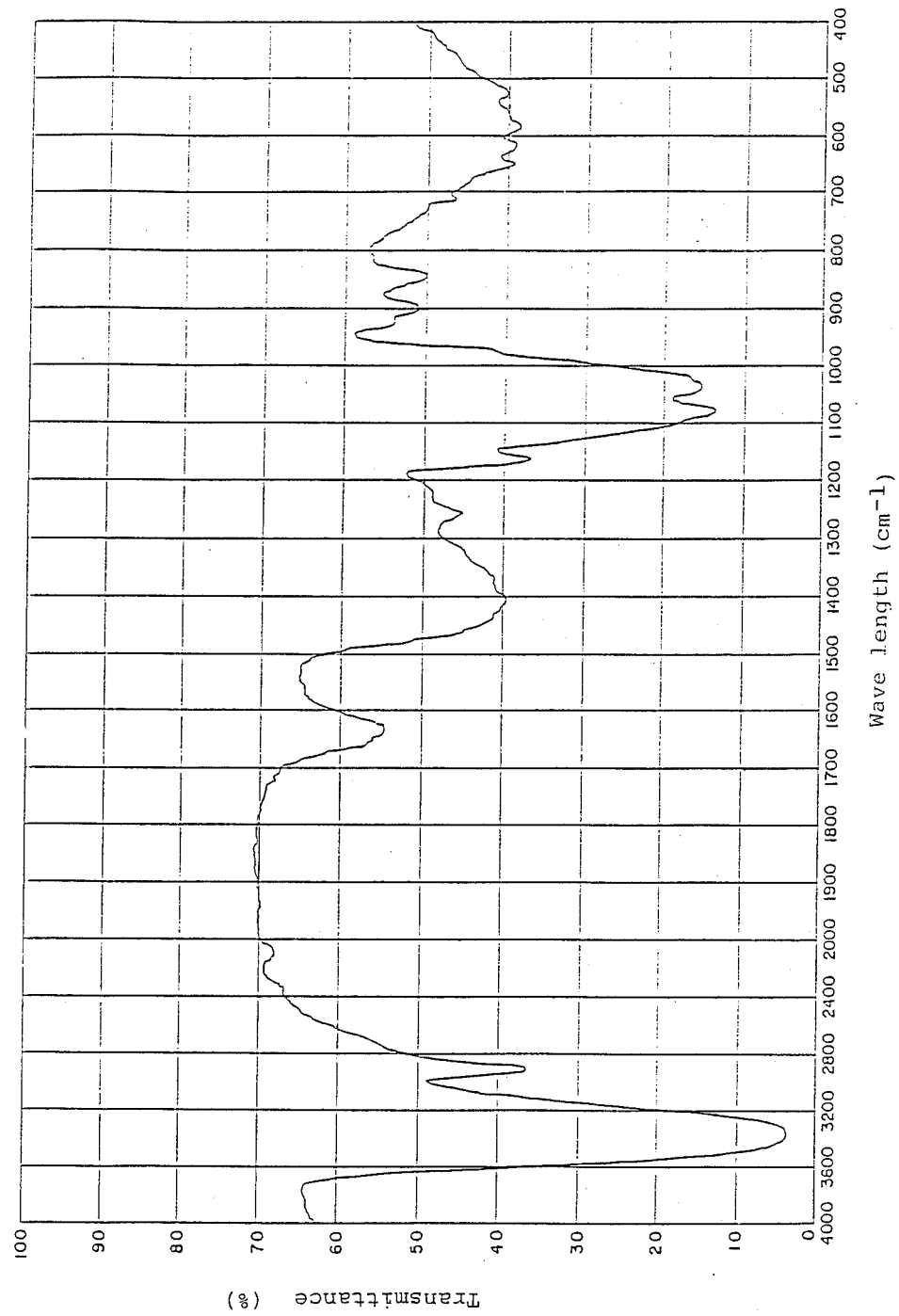

The spectrum measured by the KBr method is shown in FIG. 3. Wave numbers of main absorption peaks are shown in the following.

Figure 4:
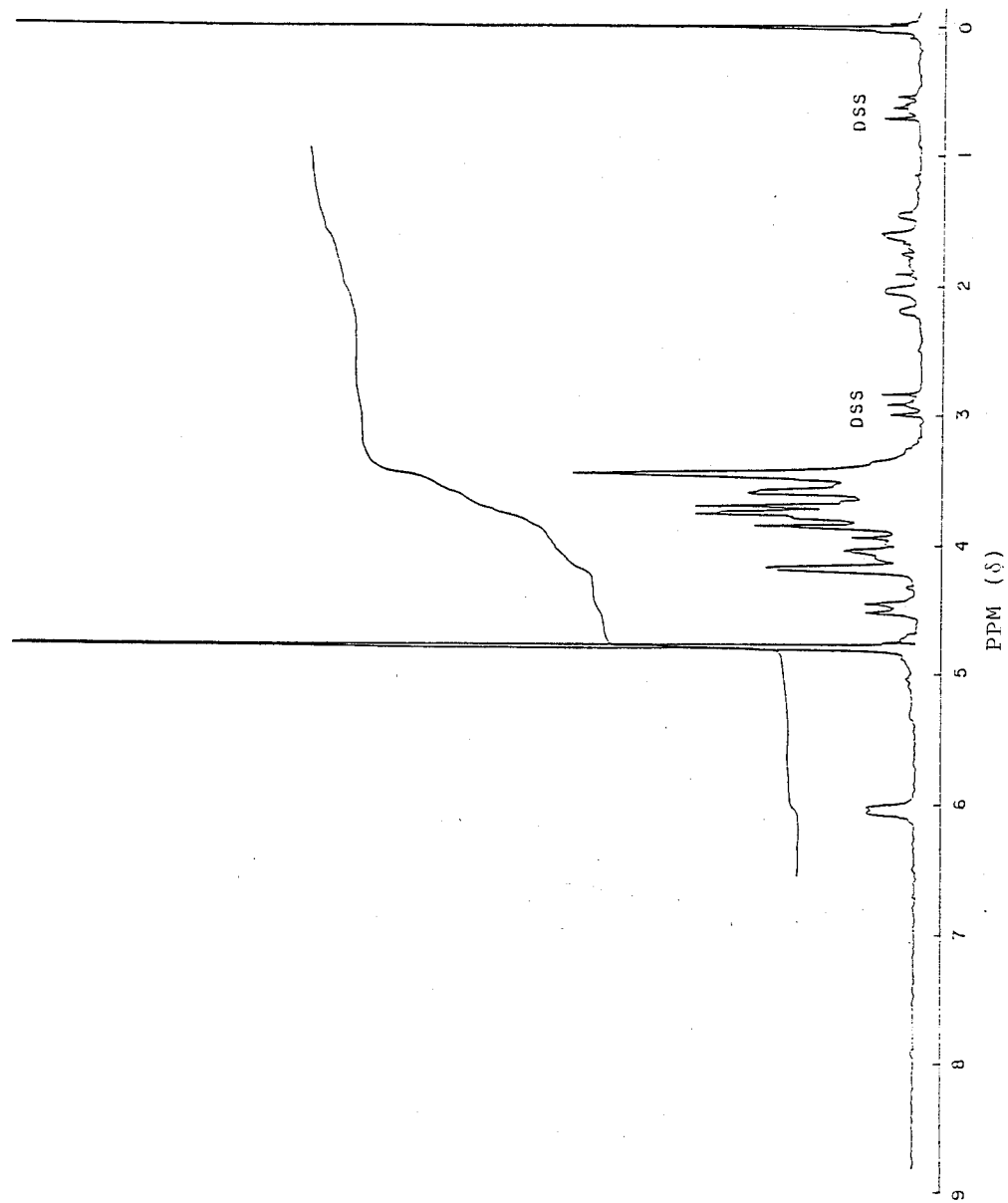

3370, 2900, 1635, 1410, 1260, 1160, 1075, 1030, 900, 845 cm$^{-1}$ (6) $^1$H-NMR spectrum Shown in FIG. 4 are the spectral data obtained in heavy water at 100 MHz (ppm; internal standard: DSS). The chemical shifts ($\delta$), splitting pattern, and coupling constant (J) were $\delta$ 1.53 (1H, dd, J=3 Hz, 15.5 Hz, H-6), 2.12 (1H, dd, J=3 Hz, 15.5 Hz, H-6), 3.30–4.20 (18H), 4.47 (1H, d, J=7.1 Hz, H-1″), and 6.04 (1H, d, J=4.6 Hz, H-2′). Chemical shift, splitting pattern, and coupling constant (J) of validamycin G undecaacetate obtained by acetylation of validamycin G with acetic anhydride-pyridine, measured in CDCl$_3$ at 400 MHz (ppm; internal standard: TMS) are shown in Table 1.

(7) $^{13}$C-NMR spectrum

Values of Chemical shifts ($\delta$) under decoupling conditions in heavy water at 100 MHz (ppm; internal standard: DSS) and splitting pattern under off-resonance conditions are shown in Table 2.

(8) Solubility in solvents

Soluble in water, dimethylsulfoxide and methanol. Slightly soluble or insoluble in ethanol, ethyl acetate, chloroform, and acetone.

(9) Color reaction

Reaction with Greig-Leaback reagent: positive
Naphthoresorcinol-sulfuric acid reaction: positive

(10) Thin layer chromatography

Rf values on TLC plate: silica gel 60F$_{254}$ (produced by Merck & Co.) developed with 1-PrOH-AcOH-H$_2$O (4:1:1) (developing solvent I) or 1-BuOH-MeOH-CHCl$_3$-28%NH$_4$OH (4:5:2:5) (developing solvent II) are listed in Table 3.

TABLE 1

$^1$H NMR (400 MHz) data of Validoxylamine G octaacetate and Validamycin G undecaacetate in CDCl$_3$ Validoxylamine G octaacetate

| Proton | Chemical shifts $\delta$* | Splitting Pattern and Coupling Constant J(Hz) |
|---|---|---|
| H-1 | 3.547 | dt J = 2.9, 3.1, 4.6 |
| H-2 | 5.018 | dd J = 4.6, 10.3 |
| H-3 | 5.613 | t J = 10.3 |
| H-4 | 5.069 | d J = 10.3 |
| H-6 | 1.688 | dd J = 2.9, 15.4 |
|  | 1.942 | dd J = 3.1, 15.4 |
| H-7 | 3.653 | ABq J = 11.4 |
|  | 4.042 |  |
| H-1′ | 3.603 | m |
| H-2′ | 5.995 | d J = 5.1 |
| H-4′ | 5.401 | d J = 6.8 |
| H-5′ | 5.435 | dd J = 6.8, 10.6 |
| H-6′ | 4.983 | dd J = 5.1, 10.6 |
| H-7′ | 4.384 | ABq J = 13.4 |
|  | 4.601 |  |
| NH | 6.594 | s |
| COCH$_3$ | 2.017 | s |
|  | 2.048 | s |
|  | 2.067 | s |
|  | 2.068 | s |
|  | 2.071 × 2 | s |
|  | 2.078 | s |
|  | 2.139 | s |
| H-1 | 3.426 | dt J = 2.7, 3.1, 4.4 |

TABLE 1-continued $^1$H NMR (400 MHz) data of Validoxylamine G octaacetate and Validamycin G undecaacetate in CDCl$_3$ Validoxylamine G octaacetate

| Proton | Chemical shifts $\delta$* | Splitting Pattern and Coupling Constant J(Hz) |
|---|---|---|
| H-2 | 4.928 | dd J = 4.4, 9.9 |
| H-3 | 5.522 | t J = 9.9, |
| H-4 | 3.665 | d J = 9.9. |
| H-6 | 1.492 | dd J = 2.7, 15.3 |
|  | 1.895 | dd J = 3.1, 15.3 |
| H-7 | 3.922 | ABq J = 11.1 |
|  | 4.127 |  |
| H-1′ | 3.598 | m |
| H-2′ | 5.973 | d J = 4.6 |
| H-4′ | 5.383 | d J = 6.6 |
| H-5′ | 5.417 | dd J = 6.6, 10.2 |
| H-6′ | 4.985 | dd J = 5.1, 10.2 |
| H-7′ | 4.371 | ABq J = 13.3 |
|  | 4.599 |  |
| H-1″ | 4.498 | d J = 9.1 |
| H-2″ | 4.967 | t J = 9.1 |
| H-3″ | 5.163 | t J = 9.1 |
| H-4″ | 5.089 | t J = 9.1 |
| H-5″ | 3.632 | ddd J = 2.3, 4.1, 9.1 |
| H-6″ | 4.037 | dd J = 2.3, 12.5 |
|  | 4.404 | dd J = 4.1, 12.5 |
| NH | 5.870 | br s |
| COCH$_3$ | 1.989 | s 2.061 s |
|  | 2.007 | s 2.065 s |
|  | 2.032 | s 2.083 s |
|  | 2.044 | s 2.102 s |
|  | 2.052 | s 2.141 s |
|  | 2.058 | s |

*Internal standard: TMS

TABLE 2

$^{13}$C NMR Spectrum of Validoxylamine G and Validamycin G

| | Chemical shifts data $\delta$ (ppm)* | |
|---|---|---|
| | Validoxylamine G | Validamycin G |
| C-1 | 56.7 (d) | 56.4 (d) |
| C-2 | 75.5 (d) | 75.4 (d) |
| C-3 | 74.3 (d) | 72.9 (d) |
| C-4 | 76.6 (d) | 86.0 (d) |
| C-5 | 78.4 (s) | 79.0 (s) |
| C-6 | 31.4 (t) | 31.8 (t) |
| C-7 | 67.8 (t) | 67.1 (t) |
| C-1′ | 54.4 (d) | 54.5 (d) |
| C-2′ | 125.3 (d) | 125.0 (d) |
| C-3′ | 142.2 (s) | 142.1 (s) |
| C-4′ | 75.6 (d) | 75.8 (d) |
| C-5′ | 74.3 (d) | 74.3 (d) |
| C-6′ | 72.4 (d) | 72.5 (d) |
| C-7′ | 64.3 (t) | 64.3 (t) |
| C-1″ |  | 105.8 (d) |
| C-2″ |  | 76.2 (d) |
| C-3″ |  | 78.5 (d) |
| C-4″ |  | 72.1 (d) |
| C-5″ |  | 78.7 (d) |
| C-6″ |  | 63.2 (t) |

*Internal standard: DSS

TABLE 3

Rf values on thin layer chromatography of Validamycin group antibiotics

| Compound | | I | II |
|---|---|---|---|
| Validoxylamine | A | 0.30 | 0.40 |
|  | B | 0.37 | 0.32 |
|  | G | 0.23 | 0.24 |
| Validamycin | A | 0.20 | 0.29 |
|  | B | 0.29 | 0.23 |
|  | C | 0.14 | 0.14 |
|  | D | 0.20 | 0.21 |
|  | E | 0.14 | 0.21 |
|  | E | 0.14 | 0.21 |

TABLE 3-continued

Rf values on thin layer chromatography of
Validamycin group antibiotics

| Compound | I | II |
|---|---|---|
| G | 0.18 | 0.14 |

Solvent system I: 1-PrOH-AcOH-H₂O (4:1:1)
II: 1-BuOH-MeOH-CHCl₃-28% NH₄OH (4:5:2:5)
Thin layer silica gel 60F$_{254}$ (Merck)

TABLE 4

[Structural formula with positions labeled: CH₂OR⁶ at 7', OH at 2, with ring positions 1'-6' and 1-7, substituents R⁵O, OH, N-H, R²R⁴OH₂C, OR³, HO, R¹]

| | |
|---|---|
| VA-A | $R^1 = R^2 = R^3 = R^4 = R^5 = R^6 = H$ |
| VA-B | $R^2 = OH, R^1 = R^3 = R^4 = R^5 = R^6 = H$ |
| VA-G | $R^1 = OH, R^2 = R^3 = R^4 = R^5 = R^6 = H$ |
| VM-A | $R^3 = \beta\text{-D-Glc}, R^1 = R^2 = R^4 = R^5 = R^6 = H$ |
| VM-B | $R^2 = OH, R^1 = R^5 = R^6 = H.$ |
| | $\beta$-D-Glc is attached to one of the hydroxyl groups in hydroxy validamine moiety, but the hydroxyl group which $\beta$-D-Glc is attached to has not been specified yet. |
| VM-C | $R^3 = \beta\text{-D-Glc}, R^6 = \alpha\text{-D-Glc}, R^1 = R^2 = R^4 = R^5 = H$ |
| VM-D | $R^4 = \alpha\text{-D-Glc}, R^1 = R^2 = R^3 = R^5 = R^6 = H$ |
| VM-E | $R^3 = \alpha\text{-D-Glc-(1}\rightarrow\text{4)-}\beta\text{-D-Glc}, R^1 = R^2 = R^4 = R^5 = R^6 = H$ |
| VM-F | $R^3 = \beta\text{-D-Glc}, R^5 = \alpha\text{-D-Glc}, R^1 = R^2 = R^4 = R^6 = H,$ |
| VM-G | $R^1 = OH, R^3 = \beta\text{-D-Glc}, R^2 = R^4 = R^5 = R^6 = H$ |

VA = Validoxylamine,
VM = Validamycin,
VE = Valienamine,
VD = Validamine,
$\alpha$-D-Glc = $\alpha$-D-glucopyranosyl,
$\beta$-D-Glc = $\beta$-D-glucopyranosyl.

Validoxylamine G and validamycin G of this invention are novel compounds which have not yet been disclosed in the literature, and are produced, for example, by the following method; *Streptomyces hygroscopicus var. limoneus* belonging to the genus Streptomyces, is cultivated under aerobic conditions to produce validoxylamine G and validamycin G.

*Streptomyces hygroscopicus var. limoneus* is deposited as IFO 12703 at Institute for Fermentation, Osaka, as FERM-P No. 468 at Fermentation Research Institute, Agency of Industrial Science and Technology, and as ATCC 21431 at The American Type Culture Collection.

As one of the common properties of microorganisms, the strain described above also can mutate spontaneously or in response to a mutagen. Mutants obtained by radiation with radiant rays such as X-rays, 65 -rays, UV-rays, etc., by single spore isolation, by treatment with various chemicals, by cultivation in the medium containing a chemical, or by other methods, and mutants occurring spontaneously, which can produce validamycin G and/or validoxylamine G may all be utilized for the method of this invention.

The media used for cultivation of the microorganisms described above in this invention may be liquid or solid as far as they contain nutrients which the strain may utilize, but liquid media are preferred in a large scale cultivation. The media are suitably admixed with the carbon and nitrogen sources that the microorganisms can assimilate and digest, inorganic substances, trace nutrients, etc. As the carbon source are used, for example, glucose, lactose, sucrose, maltose, dextrin, starch, glycerin, mannitol, sorbitol, and oils and fats (e.g. soybean oil, lard oil, chicken oil, etc.); as nitrogen source, meat extract, yeast extract, dried yeast, powdered soybean, corn steep liquor, peptone, cotton seed flour, spent molasses, urea, ammonium salts (e.g. ammonium sulfate, ammonium chloride, ammonium nitrate, ammonium acetate, etc.) and others are used. In addition, metal salts such as salts of sodium, potassium, calcium, magnesium, iron, manganese, zinc, cobalt and nickel, salts of inorganic acid such as phosphoric acid and boric acid, and salts of organic acid such as acetic acid and propionic acid are used appropriately. Further, amino acids (e.g. glutamic acid, aspartic acid, alanine, valine, lysine, methionine, proline, etc.), vitamins (e.g. $B_1$, $B_2$, nicotinic acid, $B_{12}$, C, etc.) and nucleic acids (e.g. purine and pyrimidine, and their derivatives, etc.) may be employed. Inorganic or organic acids, alkali, buffer, etc. may be added to adjust pH of the media, and suitable amounts of oils and fats, surfactants, etc. may be added as defoaming agents.

Means of cultivation include standing culture, shaken culture, and submerged culture. It is needless to say that the submerged culture is desirable for a large scale cultivation. Conditions of cultivation are of course variable depending upon the state and composition of the medium, the strain, means of cultivation, etc., but it is advisable to select the temperature of 20°–45° C. and initial pH in the range of about 6–8. Preferably the temperature at the middle stage of cultivation is 24°–37° C. with the initial pH cf 6.5–8.5. The cultivation period is also variable according to the conditions described above, but it is advisable to cultivate until the concentrations of validoxylamine G and/or validamycin G attain their maxima. The period required for this is usually about 24–192 hours, preferably 72–168 hours by shaken culture or submerged culture with use of liquid media.

For the recovery of the objective substances from the culture broth, means used usually for recovery of metabolites of microorganisms are employed solely or in combination therewith in a arbitrary order or repeatedly. That is, for example, filtration, centrifugation, concentration, drying, freeze-drying, adsorption, desorption, procedures utilizing the difference in solubilities in various solvents (e.g. precipitation, crystallization, etc.), chromatography, etc. are used. In addition, by taking advantage of the fact that validoxylamine G and validamycin G are water-soluble basic substances, use is advantageously made of the procedure employed for isolation and purification of water-soluble basic substances, e.g. chromatography and adsorption-desorption using ion-exchange resin, activated carbon, high porous polymer, cephadex, cephadex ion-exchanger, cellulose, ion-exchange cellulose, silica gel, alumina, etc.

More specifically speaking, the objective products may be obtained for example by the following processes: mycelia are removed from the culture broth by centrifugation or by filtration, followed by adsorption of the objective substances onto a chromatographic column of activated carbon desirably after the pH of the supernatant or of the filtrate is made basic, and then elution with an aqueous solution containing lower alcohols such as methanol, ethanol, n-propyl alcohol and isopropyl alcohol, n-butyl alcohol and acetone. The objective substances may be adsorbed onto cation-exchange resin (e.g. ion-exchange resin containing sulfonic acid functional group such as Dowex 50W×8 etc.) and eluted with acid (e.g. hydrochloric acid), alkali(e.g. aqueous ammonia solution of sodium hydroxide), or buffer (e.g. pyridine-acetic acid buffer). The resultant eluate is concentrated under reduced pressure, and the objective substances may be purified, if necessary, by repeated activated carbon chromatography. The objective substances may be purified and isolated by chromatography on anion exchange resin such as Dowex 1×2 (OH⁻ form) followed by elution with, for example, water.

The compounds of this invention, VA-G and VM-G, have, like other validamycin antibiotics, an activity against the sheath blight of the rice plant. For example, the minimum concentration causing the abnormal branching at the tops of hypha of Rhizoctonia solanii [See J. Antibiotics 24,114–118 (1971)] was 0.5 $\mu$g/mL for VM-G and 2.5 $\mu$g/mL for VA-G.

In addition VA-G and VM-G have also $\alpha$-glucosidase-inhibiting activity, for example, IC$_{50}$ (molarity required for 50% inhibition of the enzymatic activity when the substrate is 50 mM sucrose) against sucrase from porcine small intestine was $1.1\times10^{-4}$M for VM-G and $8.8\times10^{-6}$M for VA-G. Therefore, these compounds may be used as drugs for various diseases due to hyperglycemia, for example as anti-obesity drugs or as anti-diabetic drugs.

Furthermore, VA-G and VM-G are useful compounds as materials for production of valiolamine. That is, valiolamine may be produced, for example, by chemical degradation of VA-G and VM-G or enzymatic degradation using enzymes of microorganisms. Methods of chemical degradation include those which give valiolamine by hydrogenolysis of VA-G in the presence of a catalyst for catalytic reduction, such as platinum dioxide, platinum black, palladium black, palladium-carbon, and Raney nickel, in a solvent such as water, acetic acid-water, methanol-water, and ethanol-water. The reaction is usually performed at room temperature under atmospheric pressure, but may be performed under heating or pressure. When VM-G is a starting material, the objective valiolamine may be obtained, for example, by hydrogenolysis of VM-G, as in the case of VA-G described above, followed by hydrolysis of the resultant $\beta$-D-glucopyranosylvaliolamine.

Methods of enzymatic degradation include the treatment of VM-G or VA-G with the culture broth or the treated culture broth of microorganisms that can produce valiolamine from VM-G or VA-G, e.g. *Flavobacterium saccharophilum* (IFO 13984, FERM-P No. 5707), *Cytophaga heparina* (IFO 12017), *Agrobacterium radiobacter* (IFO 12664) and *Agrobacterium tumefaciens* (IFO 3058). "The treated culture broth" described above means bacterial cells or enzyme-containing ground cells obtained by physico-chemical treatment of the culture, e.g. filtration, centrifugation, ultrasonication, French press treatment, grinding with alumina, treatment with bacteriolytic enzymes, treatment with surfactant, treatment with organic solvent, etc.; enzymes obtained by known purification by prior art methods of purification such as filtration, centrifugation, ammonium sulfate fractionation, dialysis, chromatography, electrophoresis, and gel filtration of the ground cells; and the cells or enzymes immobilized by known methods.

Valiolamine is a potent $\alpha$-glucosidase-inhibitor and in addition it is an important compound as the starting material for more potent $\alpha$-glucosidase-inhibitors, N-substituted valiolamine derivatives (European Patent Publication No. 56194 and 89812).

The N-substituted valiolamine derivatives having potent $\alpha$-glucosidase-inhibitory action include:
(1) N-phenethylvaliolamine,
(2) N-(3-phenylallyl)valiolamine,
(3) N-furfurylvaliolamine,
(4) N-thenylvaliolamine,
(5) N-(3-pyridylmethyl)valiolamine,
(6) N-(4-bromobenzyl)valiolamine,
(7) N-[(R)-$\beta$-hydroxyphenethyl]valiolamine,
(8) N-[(S)-$\beta$-hydroxyphenethyl]valiolamine,
(9) N-($\beta$-hydroxy-2-methoxyphenethyl)valiolamine,
(10) N-(3,5-di-tert-butyl-4-hydroxybenzyl)valiolamine,
(11) N-(cyclohexylmethyl)valiolamine,
(12) N-geranylvaliolamine,
(13) N-(1,3-dihydroxy-2-propyl)valiolamine,
(14) N-(1,3-dihydroxy-1-phenyl-2-propyl)valiolamine,
(15) N-[(R)-o-(hydroxymethyl)benzyl]valiolamine,
(16) N-cyclohexylvaliolamine,
(17) N-(2-hydroxycyclohexyl)valiolamine,
(18) N-[(1R,2R)-2-hydroxycyclohexyl]valiolamine,
(19) N-(2-hydroxycyclopentyl)valiolamine,
(20) Methyl 4-[(1S,2S)-(2,4,5(OH)/3,5)-2,3,4,5-tetrahydroxy-5-(hydroxymethyl)cyclohexyl]amino-4,6-dideoxy-$\alpha$-D-glucopyranoside,
(21) Methyl 4-[(1S,2S)-(2,4,5(OH)/3,5)-2,3,4,5-deoxy-$\alpha$-D-glucopyranoside,
(22) [(1S,2S)-(2,4,5(OH)/3,5)-2,3,4,5-tetrahydroxy-5-(hydroxymethyl)cyclohexyl][(1R,2S)-(2,6/3,4)-4-amino-2,3-dihydroxy-6-(hydroxymethyl)cyclohexyl]-amine,
(23) N-[(1R,2S)-(2,4/3,5)-2,3,4-trihydroxy-5-(hydroxymethyl)cyclohexyl]valiolamine,
(24) N-[(1R,2S)-(2,6/3,4)-4-amino-2,3-dihydroxy-6-methylcyclohexyl]valiolamine,
(25) N-[(1R,2S)-(2,6/3,4)-2,3,4-trihydroxy-6-methylcyclohexyl]valiolamine,
(26) N-[(1R,2S)-(2,4,6/3)-2,3,4-trihydroxy-6-methylcyclohexyl]valiolamine,
(27) 4-O-$\alpha$-[4-[[(1S)-(1,2,4,5(OH)/3,5)-2,3,4,5-tetrahydroxy-5-(hydroxymethyl)cyclohexyl]amino]-4,6-dideoxy-D-glucopyranosyl]-D-glucopyranose,
(28) 1,6-anhydro-4-O-$\alpha$-[4[[;(1S)-(1,2,4,5)OH)/3,5)-2,3,4,5-tetrahydroxy-5-(hydroxymethyl)cyclohexyl]-amino]-4,6-dideoxy-D-glucopyranosyl]-$\beta$-D-glucopyranose.

The invention is illustrated by reference examples and examples.

REFERENCE EXAMPLE 1

Validoxylamine G (100 mg) was dissolved in 0.05 M phosphate buffer (pH 7.0) (20 mL) and wet cells of *Flavobacterium saccharophilum* IFO 13984 (about 2 g) were added to the solution, followed by incubation at 27° C. for 24 hours with stirring. The reaction mixture was centrifuged for removal of cells, and the supernatant was adsorbed onto a column (50 mL) of Amberlite IRC-50 (NH$_4^+$ form, manufactured by Rohm & Haas Co.), followed by washing with water and elution aqueous ammonia. The eluate was concentrated to dryness under reduced pressure, and the residue was adsorbed again onto a column (50 mL) of Amberlite IRC-50

($NH_4^+$ form) and eluted with 0.1N aqueous ammonia. In succession to the fractions containing valienamine (eluate fractions 120-140 mL), the fractions containing valiolamine were eluted (eluate fractions 340-430 mL). The fractions containing valiolamine were concentrated to dryness under reduced pressure, and the residue was submitted to column chromatography on Dowex 1×2 ($OH^-$ form, manufactured by Dow Chemicals Co.; 2 mL) followed by concentration of the eluate to dryness under reduced pressure, to give white powders of valiolamine (35 mg).

REFERENCE EXAMPLE 2

In the manner of Reference Example 1, validamycin G (150 mg) was submitted to enzymatic degradation using wet cells of *Flavobacterium saccharophilum* IFO 13984 (about 2 g), to give a white powder of valiolamine (34 mg).

REFERENCE EXAMPLE 3

An aqueous solution (50 mL) of validoxylamine G (420 mg) was submitted to catalytic reduction at room temperature under atmospheric pressure in the presence of platinum oxide (20 mg). The catalyst was removed by filtration, and the filtrate was adsorbed onto a column of Amberlite CG-50 ($NH_4^-$ form, 50 mL) followed by washing with water and then elution with 0.5N aqueous ammonia (200 mL). The eluate was concentrated under reduced pressure, and submitted to column chromatography on Dowex 1×2 ($OH^-$ form, 100 mL) and eluted with water. The eluate fractions (120-200 mL) were concentrated to dryness under reduced pressure, to give white powders of valiolamine (60 mg).

REFERENCE EXAMPLE 4

An aqueous solution (30 mL) of validamycin G (106 mg) was submitted to catalytic reduction at room temperature under atmospheric pressure in the presence of platinum oxide (10 mg). The catalyst was removed by filtration and the filtrate was adsorbed onto a column of Amberlite CG-50 ($NH_4^+$ form, 30 mL) followed by washing with water and then elution with 0.5N aqueous ammonia. The eluate was concentrated to dryness under reduced pressure, and the residue was dissolved in 1N sulfuric acid (20 mL) and hydrolyzed at 80° C. for 10 hours. The reaction mixture was neutralized with barium hydroxide and the supernatant obtained by centrifugation was concentrated under reduced pressure. The concentrate was adsorbed onto a column of Amberlite CG-50 (ammonium form, 20 mL) followed by washing with water and then elution with 0.5N aqueous ammonia. The eluate was concentrated under reduced pressure and submitted to column chromatography on Dowex 1×2 ($OH^-$ form, 100 mL) followed by elution with water. The eluate fractions were concentrated under reduced pressure and then freeze-dried, to give a white powder of valiolamine (11 mg).

EXAMPLE 1

(a) In the medium (glucose 3%, soybean flour 2.2%, peptone 0.3%, calcium carbonate 0.4%, water 500 mL, pH 7) in a sterilized 2L Sakaguchi flask, a loopful of *Streptomyces hygroscopicus var. limoneus* (IFO 12703, Ferm 468, ATCC 21431) cultivated on glucose-asparagine agar medium was inoculated and incubated at 28° C for 48 hours on a rotary shaker. Five hundred mL of the culture was transferred to the medium (glucose 5%, soybean flour 3.6%, peptone 0.5%, calcium carbonate 0.4%, water 30 L, pH 7) in a sterilized 50 L stainless steel fermentation tank and incubated at 28° C for 114 hours by submerged culture. The resultant culture was filtered after pH adjustment to 9 and addition of filter aid, and the filtrate (25 L) was adsorbed onto a column (10 L) of activated carbon followed by washing with water and elution with 7% n-butyl alcohol-water. The eluate was concentrated to dryness under reduced pressure, to give 123 g of a crude powder.

(b) One hundred grams of the crude powder containing validamycin G and validoxylamine G obtained in Example 1a) was submitted to column chromatography on Dowex 1×2 ($OH^-$ form, manufactured by Dow Chemicals; 1.8L), eluted with water to give validoxylamine G-containing fractions (eluate fractions 3-5 L; abbreviated as eluate fraction I' hereafter) and validamycin G-containing fractions (eluate fractions 6-8 L; abbreviated as 'eluate fraction II' hereafer). The eluate fraction I and the eluate fraction II were separately concentrated to dryness to give 2.7 and 3.0 g of a crude powder, respectively. The crude powder from the eluate fraction I (2.7 g) was submitted to column chromatography on Dowex 50W x 8 (pyridine form, manufactured by Dow Chemicals Co.; 200 mL) and eluted with 0.2 M pyridine-acetate buffer (pH 6.0). In succession to the fractions containing validoxylamine B and validamycin D (eluate fractions 100-420 mL), validoxylamine G-containing fractions (eluate fractions 520-1140 mL) were eluted. The validoxylamine G-containing eluate fractions were concentrated to dryness under reduced pressure, to give a white powder (0.8 g) of validoxylamine G.

The crude powder from the eluate fraction II (3.0 g) were submitted to column chromatography on Dowex 50W×8 (pyridine form, 200 mL) and eluted with 0.2M pyridine-acetate buffer (pH 6.0). In succession to the validamycin C-containing fractions (eluate fractions 120-220 mL) validamycin G-containing fractions (eluate fractions 460-620 mL) were eluted. The validamycin G-containing fractions were concentrated to dryness under reduced pressure, and the residue was submitted to column chromatography on Dowex 1 x 2 (OH- form, 50 mL) and eluted with water. The validamycin G-containing fractions were concentrated to dryness under reduced pressure, to give a white powder of validamycin G (0.6 g).

What is claimed is:

1. A valiolamine derivative of the formula:

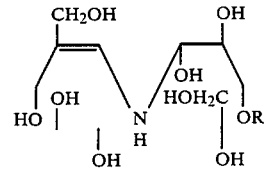

where R stands for hydrogen or β-D-glucopyranosyl group.

2. A valiolamine derivative according to claim 1, wherein R stands for hydrogen, namely, validoxylamine G.

3. A valiolamine derivatives of the formula:

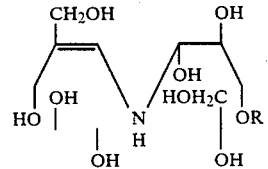

where R stands for β-D-glucopyranosyl.

* * * * *

UNITED STATES PATENT AND TRADEMARK OFFICE
CERTIFICATE OF CORRECTION

PATENT NO. : 4,923,975  Page 1 of 2

DATED : May 8, 1990

INVENTOR(S) : Yukihiko KAMEDA et al.

It is certified that error appears in the above-identified patent and that said Letters Patent is hereby corrected as shown below:

ON TITLE PAGE:
　　The formulas in the ABSTRACT, column 1, claim 1 and claim 3 should be amended to:

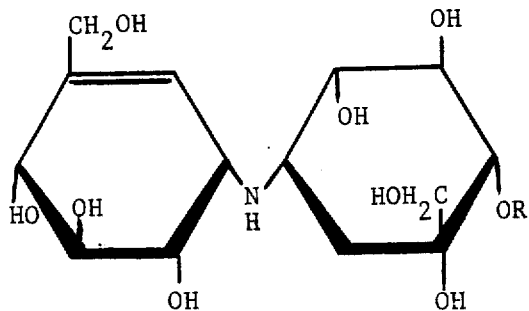

UNITED STATES PATENT AND TRADEMARK OFFICE
CERTIFICATE OF CORRECTION

PATENT NO. : 4,923,975

DATED : May 8, 1990

INVENTOR(S) : Yukihiko KAMEDA et al.

It is certified that error appears in the above-identified patent and that said Letters Patent is hereby corrected as shown below:

The formula in column 5 should be amended to:

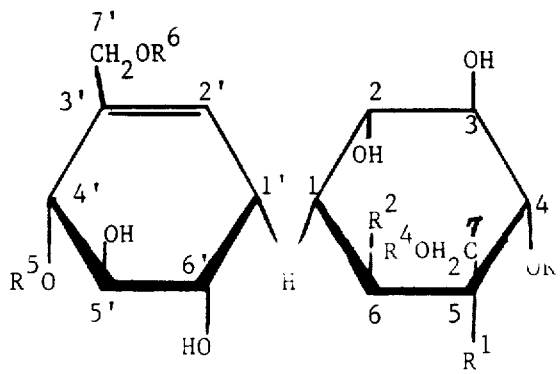

Signed and Sealed this

Nineteenth Day of November, 1991

Attest:

HARRY F. MANBECK, JR.

Attesting Officer

Commissioner of Patents and Trademarks